United States Patent
Kotian et al.

(10) Patent No.: US 11,382,594 B2
(45) Date of Patent: Jul. 12, 2022

(54) SYSTEMS AND METHODS FOR INTERVENTIONAL RADIOLOGY WITH REMOTE PROCESSING

(71) Applicant: General Electric Company, Schenectady, NY (US)

(72) Inventors: Francois Kotian, Villepreux (FR); Francisco Sureda, Chatenay-Malabry (FR)

(73) Assignee: General Electric Company, Schenectady, NY (US)

( * ) Notice: Subject to any disclaimer, the term of this patent is extended or adjusted under 35 U.S.C. 154(b) by 58 days.

(21) Appl. No.: 16/237,212

(22) Filed: Dec. 31, 2018

(65) Prior Publication Data

US 2020/0205769 A1    Jul. 2, 2020

(51) Int. Cl.
*A61B 6/00* (2006.01)
*G16H 30/20* (2018.01)
*G16H 30/40* (2018.01)
*A61B 6/03* (2006.01)

(52) U.S. Cl.
CPC .............. *A61B 6/563* (2013.01); *A61B 6/032* (2013.01); *A61B 6/461* (2013.01); *G16H 30/20* (2018.01); *G16H 30/40* (2018.01)

(58) Field of Classification Search
CPC .......................... G06K 7/1099; G03F 7/20–70
See application file for complete search history.

(56) References Cited

U.S. PATENT DOCUMENTS

| | | | |
|---|---|---|---|
| 6,459,765 B1 * | 10/2002 | Ganin | A61B 6/00 378/108 |
| 7,991,837 B1 * | 8/2011 | Tahan | G06F 3/0481 348/240.3 |
| 8,526,573 B2 | 9/2013 | Ferro, Jr. | |
| 9,111,016 B2 | 8/2015 | Besson et al. | |
| 9,224,180 B2 | 12/2015 | Macoviak et al. | |
| 2001/0017909 A1 * | 8/2001 | Doubrava | A61B 6/032 378/7 |
| 2004/0030585 A1 | 2/2004 | Sariel | |
| 2006/0203729 A1 * | 9/2006 | Deshpande | H04L 1/24 370/235 |

(Continued)

OTHER PUBLICATIONS

The DICOM Standard (https://people.cas.sc.edu/rorden/dicom/index.html, first published Apr. 2016 (Year: 2016).*

(Continued)

*Primary Examiner* — Mark Roz (57) ABSTRACT

Various systems and methods are provided for interventional imaging with remote processing. In one embodiment, a method for an imaging system comprises, during a scan, transmitting data to a remote computing system, controlling the imaging system according to results of remote processing of the data via the remote computing system responsive to receiving the results of the remote processing before a latency deadline, and controlling the imaging system according to results of local processing at the imaging system responsive to receive the results of the remote processing after the latency deadline. In this way, improved or enhanced images may be processed remotely and displayed to a user in real-time during an interventional procedure, and locally-processed images may be displayed if the remote processing is delayed.

20 Claims, 6 Drawing Sheets

(56) References Cited

U.S. PATENT DOCUMENTS

| | | | |
|---|---|---|---|
| 2006/0293581 A1* | 12/2006 | Plewes | A61K 49/0419 |
| | | | 600/407 |
| 2009/0149867 A1* | 6/2009 | Glozman | A61B 34/70 |
| | | | 606/130 |
| 2015/0356757 A1 | 12/2015 | Marshall | |
| 2016/0058406 A1 | 3/2016 | Lee | |
| 2016/0140702 A1* | 5/2016 | Kindle | H04N 5/23216 |
| | | | 382/167 |

OTHER PUBLICATIONS

EP application 19220104.4 filed Dec. 31, 2019—Search Report dated May 8, 2020, 7 pages.

* cited by examiner

SYSTEMS AND METHODS FOR INTERVENTIONAL RADIOLOGY WITH REMOTE PROCESSING

FIELD

Embodiments of the subject matter disclosed herein relate to interventional imaging, and more particularly, to remote processing for interventional imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior or the human body or of other imaged structures).

For interventional radiology, providers such as surgeons or radiologists utilize non-invasive imaging technologies to image the internal structures while performing a minimally-invasive procedure, such as inserting a stent or guiding a catheter tube. For example, an x-ray fluoroscopy imaging system may be used to detect a foreign body, such as a catheter tube, within a patient's body so that the surgeon or radiologist may accurately position it with respect to specific anatomic structures.

BRIEF DESCRIPTION

In one embodiment, a method for an imaging system comprises, during a scan, transmitting data to a remote computing system, controlling the imaging system according to results of remote processing of the data via the remote computing system responsive to receiving the results of the remote processing before a latency deadline, and controlling the imaging system according to results of local processing at the imaging system responsive to receive the results of the remote processing after the latency deadline. In this way, improved or enhanced images may be processed remotely and displayed to a user in real-time during an interventional procedure, and locally-processed images may be displayed if the remote processing is delayed.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of interventional imaging. In particular, systems and methods are provided for enhancing the processing capabilities of an imaging system for interventional procedures. During an interventional session, a healthcare provider such as a surgeon or an interventional radiologist performs an interventional procedure on a subject such as a patient. An interventional procedure typically comprises a minimally-invasive procedure wherein the provider uses non-invasive image guidance such as x-ray fluoroscopy, ultrasound, computed tomography (CT), magnetic resonance imaging (MRI), and so on, as a guide while precisely manipulating medical tools such as needles, fine catheter tubes, and/or wires to navigate within the body. Examples of interventional procedures include, but are not limited to, angiography, balloon angioplasty, embolization, abscess drainage, needle biopsy, stent, and so on. As interventional procedures require precise manipulation of the medical tool inserted into the body, the provider relies on accurate and instantaneous imaging of the medical tool within the body.

Figure 1:
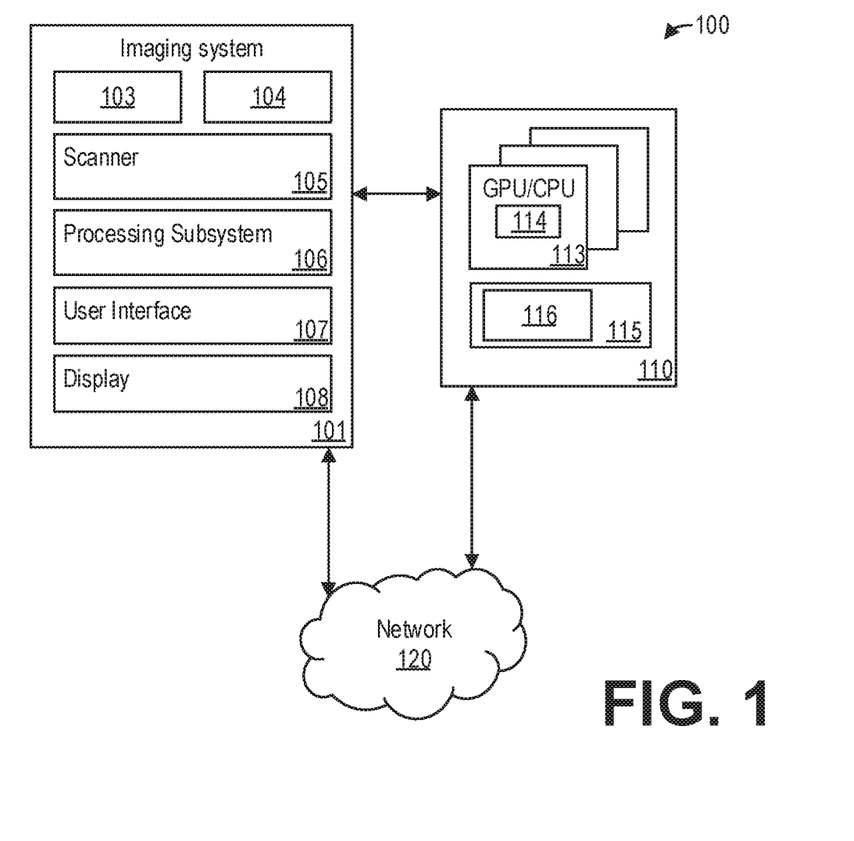
FIG. 1 shows a block schematic diagram of a simplified example system for extending the capabilities of an imaging system according to an embodiment.

To enhance the imaging capabilities of an imaging system for interventional procedures, a system for interventional radiology, such as the system depicted in FIG. 1, includes an imaging system, such as an x-ray imaging system, coupled to an edge computing system (ECS). The imaging system may transmit or stream imaging data or other data to the ECS during a scan or examination for enhanced processing during the scan, and thus the ECS extends the processing capabilities of the imaging system. However, during an interventional procedure, the timing or latency of the enhanced processing should not be excessive such that the image displayed to the provider is delayed or frozen. For example, if the results of the enhanced processing by the ECS are returned too slowly, the display of the internal anatomy may be delayed while the provider may mistakenly assume that the display is not delayed, thereby potentially causing confusion or errors in manipulating the medical tool.

Figure 2:
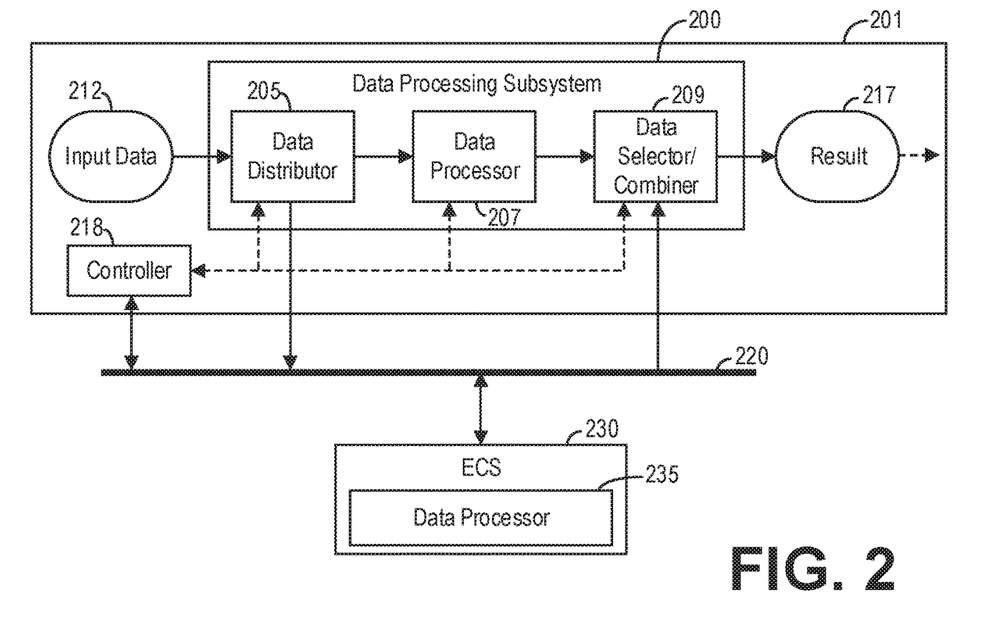
FIG. 2 shows an example architecture for a data processing subsystem according to an embodiment.

To avoid latency errors, a data processing subsystem of the imaging system, such as the data processing subsystem depicted in FIG. 2, locally processes input data while the ECS remotely processes the input data, and the data processing subsystem selects or combines the locally-processed input data or the remotely-processed input data for controlling the imaging system. As a more specific implementation of a data processing subsystem, an image processing subsystem of the imaging system, such as the image processing subsystem depicted in FIG. 3, locally processes imaging data acquired by the imaging system while the ECS remotely processes the imaging data, and the imaging processing subsystem selects or combines the locally-processed imaging data or the remotely-processed imaging data for display. A method for selecting the local or remote results, such as the method depicted in FIG. 4, includes controlling the imaging system according to the local results if the remote results are received after a latency deadline and controlling the imaging system according to the remote results if the remote results are received before the latency deadline. As non-limiting examples, controlling the imaging system according to the local or remote results includes displaying an image processed locally or an image with enhanced image processing from the ECS, as depicted in FIG. 5. Another method, such as the method depicted in FIG. 6, includes controlling the x-ray source with exposure parameters determined locally or enhanced exposure control as determined remotely. In some examples, such as the method depicted in FIG. 7, the ECS may adjust the enhanced processing to maintain latency and throughput, for example by reducing resolution or quality, and furthermore the local and remote results may be combined according to the latency.

An edge computing system (ECS) is connected to an imaging system/scanner. The ECS includes CPUs/GPUs running one or more virtual machines (VMs) configured for different types of tasks. Data is streamed in real-time from the scanner to the ECS which processes the data (in image and/or projection space) and returns the results. In this way, the imaging system appears to have additional processing power because the post-processing performed by the ECS may be output alongside or in place of reconstructed images at the display of the imaging system.

FIG. 1 shows a block schematic diagram of an example system 100 for extending the capabilities of an imaging system 101 with an edge computing system (ECS) 110 according to an embodiment. The imaging system 101 may comprise any suitable non-invasive imaging system, including but not limited to an x-ray imaging system, a computed tomography (CT) imaging system, a positron emission tomography (PET) imaging system, a magnetic resonance imaging (MRI) system, an ultrasound system, and combinations thereof (e.g., a multi-modality imaging system such as a PET/CT imaging system).

The imaging system 101 includes a processor 103 and a non-transitory memory 104. One or more methods described herein may be implemented as executable instructions in the non-transitory memory 104 that when executed by the processor 103 cause the processor 103 to perform various actions. Such methods are described further herein with regard to FIGS. 3-5.

The imaging system 101 further comprises a scanner 105 for scanning a subject such as a patient to acquire imaging data. Depending on the type of imaging system 101, the scanner 105 may comprise multiple components necessary for scanning the subject. For example, if the imaging system 101 comprises an x-ray imaging system, the scanner 105 may comprise an x-ray source and an x-ray detector mounted opposite each other on a C-arm gantry, as well as various components for controlling the x-ray source, the x-ray detector, and the C-arm gantry. As another example, if the imaging system 101 comprises a CT imaging system, the scanner 105 may comprise a CT tube and a detector array, as well as various components for controlling the CT tube and the detector array. As yet another example, if the imaging system 101 comprises an ultrasound imaging system, the scanner 105 may comprise an ultrasound transducer. Thus, the term "scanner" as used herein refers to the components of the imaging system which are used and controlled to perform a scan of a subject.

The type of imaging data acquired by the scanner 105 also depends on the type of imaging system 101. For example, if the imaging system 101 comprises a CT imaging system, the imaging data acquired by the scanner 105 may comprise projection data. Similarly, if the imaging system 101 comprises an ultrasound imaging system, the imaging data acquired by the scanner 105 may comprise analog and/or digital echoes of ultrasonic waves emitted into the subject by the ultrasound transducer.

In some examples, the imaging system 101 includes a processing subsystem 106 for managing the local and remote processing of data such as image data acquired by the imaging system 101. In some examples, the processing subsystem 106 may comprise a data processing subsystem, as described further herein with regard to FIG. 2, configured to process data acquired by and/or generated by the imaging system 101. The results of processing the data may be used to control the imaging system 101. For example, the processing subsystem 106 may process image data and/or position data of various components of the scanner 105 to perform anti-collision management. Additionally or alternatively, the processing subsystem 106 may comprise an image processing subsystem, as described further herein with regard to FIG. 3, configured to process image data for display. Although the processing subsystem 106 is depicted as a separate component from the non-transitory memory 104, it should be understood that in some examples the processing subsystem 106 may comprise a software module stored in non-transitory memory 104 as executable instructions that when executed by the processor 103 causes the processor 103 to process data or image data as described herein.

The imaging system 101 further comprises a user interface 107 configured to receive input from an operator of the imaging system 101 as well as display information to the operator. To that end, user interface 107 may comprise one or more of an input device, including but not limited to a keyboard, a mouse, a touchscreen device, a microphone, and so on.

In some examples, the imaging system 101 further comprises a display 108 for displaying images acquired via the imaging system 101 as well as other information. As an example, the display 108 may display images acquired via the imaging system 101 and processed with the image processing subsystem 106 and/or remotely processed by an ECS 110.

The system 100 further comprises an edge computing system (ECS) 110 that is communicatively coupled to the imaging system 101 via a wired or wireless connection, or in some examples is communicatively coupled via a network 120. The ECS 110 comprises a plurality of processors 113 running one or more virtual machines (VMs) 114 configured for different types of tasks. The plurality of processors 113 comprises one or more graphics processing units (GPUs) and/or one or more central processing units (CPUs). The ECS 110 further comprises a non-transitory memory 115 storing executable instructions 116 that may be executed by one or more of the plurality of processors 113. As one example, the executable instructions 116 may comprise a data processing module and/or an image processing module for processing data, such as image data, streamed from the imaging system 101 during an interventional session. The data and/or image processing module may process data similarly to the processing subsystem 106, or may process the data in a more sophisticated fashion than the processing subsystem 106. For example, whereas the processing subsystem 106 may process image data to perform basic noise reduction, the image processing module of the ECS 110 may process the image data with a more robust but computationally-expensive noise reduction algorithm, and additionally may perform enhanced image processing such as detecting and highlighting a medical tool in the image data.

Thus, as discussed further herein, data acquired by or generated by the imaging system 101 is transmitted to the ECS 110 during an interventional scan. The data may be transmitted directly or via the network 120, as non-limiting examples. The processing subsystem 106 processes the data locally at the imaging system 101, while the ECS 110 executes the executable instructions 116 via the plurality of processors 113 to process the data remotely at the ECS 110. The ECS 110 returns the results of the enhanced processing to the imaging system 101. The processor 103, for example, then controls the imaging system 101 according to the enhanced results from the ECS 110 if the enhanced results are received within a latency deadline. Otherwise, the processor 103 controls the imaging system 101 according to the local results from the processing subsystem 106.

FIG. 2 shows an example architecture for a data processing subsystem 200 according to an embodiment. The data processing subsystem 200 is within an imaging system 201, which may comprise the imaging system 101 of FIG. 1. The data processing subsystem 200 receives input data 212 and outputs one or more results 217 for controlling the imaging system 201. The data processing subsystem 200 includes a data distributor 205, a data processor 207, and a data selector/combiner 209. The data processing subsystem 200 may be implemented in the imaging system 201 as a software subsystem, such that the data distributor 205, the data processor 207, and/or the data selector/combiner 209 comprise software modules stored in non-transitory memory of the imaging system 201 and executed by one or more processors of the imaging system 201. Additionally or alternatively, one or more components of the data processing subsystem 200 may be implemented as hardware components. As an illustrative and non-limiting example, one or more of the data distributor 205, the data processor 207, and the data selector/combiner 209 may be implemented as a dedicated processor and/or memory specially configured to perform the actions described herein.

The data distributor 205 receives the input data 212 and distributes the input data 212 to the data processor 207. The data distributor 205 further distributes the input data 212 to a data processor 235 of an ECS 230, which may comprise the ECS 110 of FIG. 1, via a network 220. Prior to distribution, the data distributor 205 may tag the input data 212 with one or more of an identifier, an NTP-type timestamp, and a header containing acquisition parameters.

The data processor 207 performs local processing of the input data 212 in real-time with guaranteed latency. Such processing may include, as non-limiting examples, noise reduction, segmentation, automatic labeling, interventional device visibility enhancement, image registration and fusion, and so on. The remote image processing performed by the data processor 235 of the ECS 230 may comprise enhanced or more computationally-expensive data processing, which may include noise reduction, enhanced image quality characteristics, interventional device visibility enhancement, image registration and fusion, and so on as non-limiting examples. The data processor 235 of the ECS 230 may therefore comprise the executable instructions 116 of the ECS 110 as described hereinabove with regard to FIG. 1.

The results of the remote data processing by data processor 235 and the results of the local data processing by data processor 207 are provided to the data selector/combiner 209. The data selector/combiner 209 selects and/or combines the results from the data processors 207 and 235 according to a latency deadline. In one example, the latency comprises the time difference between receiving the local results from the data processor 207 and the remote results from the data processor 235. The latency deadline may comprise, as an illustrative and non-limiting example, 80 milliseconds. The latency deadline may be predetermined such that there is no human-perceivable difference if a remote result is received at the latency deadline and used to control the imaging system 201 instead of the local result.

The data selector/combiner 209 thus receives a stream of results from both the internal data processor 207 and, via the network 220, the remote data processor 235, associates the network result with the internally-processed result, assess network processing latency, outputs the internally-processed result to the controller 218, for example, if the network processing latency exceeds the threshold or deadline, and outputs the externally-processed result if the latency does not exceed the defined upper limit or deadline (and possibly other criteria).

Further, in some examples the data processor 235 may adjust the enhanced processing in order to meet the latency deadline. For example, if bandwidth of the network 220 or another technical matter prevents the remote results from returning to the data processing subsystem 200 within the latency deadline, the data processor 235 may reduce the resolution or otherwise adjust the enhanced processing such that the remote results may be returned to the data processing subsystem 200 within the latency deadline. For example, the subsystem 200 may be adapted to perform anti-collision management, patient dose mapping, exposure control, motion control, and so on, while the ECS 230 may perform an enhanced version of the data processing. As an example, for anti-collision management, the data processor 207 processes positions of various components of the scanner 105 with respect to the patient. The data processor 207 may use a simple model of the scanner 105 to predict, for example, future positions of the various components according to the received positions, and adjust the motion of the components accordingly. Meanwhile, the data processor 235 processes the positions of the various components of the scanner 105 with a more detailed three-dimensional model. To meet the latency deadline, the data processor 235 may, in some examples, adjust the granularity of the mesh model such that the prediction of collision may be performed more accurately and quickly when bandwidth issues or allocation of computer resources affect the latency deadline.

In some examples, the data selector/combiner 209 may selectively combine the local results and the remote results according to the adjustment of the remote processing. For example, to meet the latency deadline, the data processor 235 may only apply enhanced image processing to a given region of interest (ROI) of the input data 212, which may be centered in the image, for example. The data selector/combiner 209 may then combine the enhanced processing of the ROI of the input data 212 from the data processor 235 with the remainder of the input data 212 from the data processor 207, such that the output result 217 comprises a combination of the local and remote results.

Figure 3:
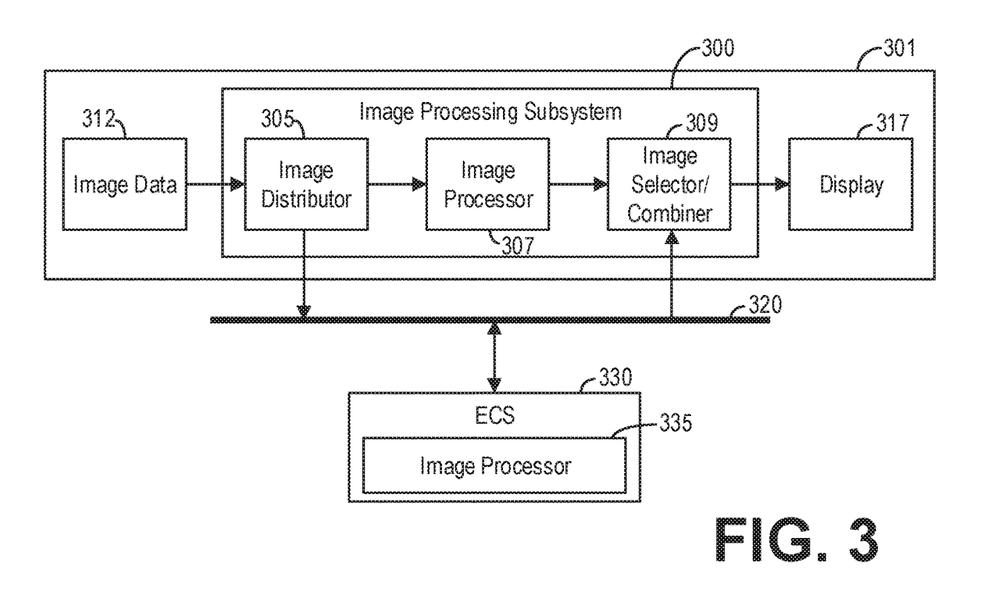
FIG. 3 shows an example architecture for an image processing subsystem according to an embodiment.

While the architecture of the data processing subsystem 200 is described with regard to data processing in general, it should be appreciated that the subsystem may be adapted to perform image processing in particular. As an illustrative example, FIG. 3 shows an example architecture for an image processing subsystem 300 according to an embodiment. The image processing subsystem 300 is within an imaging system 301, which may comprise the imaging system 101 of FIG. 1. The image processing subsystem 300 receives image data 312 and outputs one or more images to a display 317. The image processing subsystem 300 includes an image distributor 305, an image processor 307, and an image selector/combiner 309. The image distributor 305 receives the image data 312 and distributes the image data 312 to the image processor 307. The image distributor 305 further distributes the image data 312 to an image processor 335 of an ECS 330, which may comprise the ECS 110 of FIG. 1, via a network 320. Prior to distribution, the image distributor 305 tags the image data 312 with an identifier, an NTP-type timestamp, and a header containing acquisition parameters.

The image processor 307 performs local processing of the image data 312 in real-time with guaranteed latency. Such processing may include, as non-limiting examples, noise reduction, segmentation, automatic labeling, interventional device visibility enhancement, image registration and fusion, and so on. The remote image processing performed by the image processor 335 of the ECS 330 may comprise enhanced or more computationally-expensive image processing, which may include noise reduction, enhanced image quality characteristics, interventional device visibility enhancement, image registration and fusion, and so on as non-limiting examples.

The results of the remote image processing by image processor 335 and the results of the local image processing by image processor 307 are provided to the image selector/combiner 309. The image selector/combiner 309 selects and/or combines images from the image processors 307 and 335 according to a latency deadline. The latency comprises the time difference between receiving the local results from the image processor 307 and the remote results from the image processor 335. The latency deadline may comprise, as an illustrative and non-limiting example, 80 milliseconds. The latency deadline may be predetermined such that there is no human-perceivable difference if a remote result is received at the latency deadline and displayed by the display 317 instead of the local result.

The image selector/combiner 309 thus receives a stream of images from both the internal image processor 307 and the network 320, associates the network image with the internally-processed image, assess network processing latency, sends the internally-processed image to the display 317 if the network processing latency exceeds the threshold or deadline, and displays the externally-processed image if the latency does not exceed the defined upper limit or deadline (and possibly other criteria).

Further, in some examples the image processor 335 may adjust the enhanced processing in order to meet the latency deadline. For example, if bandwidth of the network 320 or another technical matter prevents the remote results from returning to the image processing subsystem 300 within the latency deadline, the image processor 335 may reduce the resolution or otherwise adjust the enhanced processing such that the remote results may be returned to the image processing subsystem 300 within the latency deadline. In such examples, the image selector/combiner 309 may selectively combine the local results and the remote results according to the adjustment of the remote processing. For example, to meet the latency deadline, the image processor 335 may only apply the enhanced image processing to a given region of interest (ROI) of the image data 312, which may be centered in the image, for example. The image selector/combiner 309 may then combine the enhanced processing of the ROI of the image data 312 from the image processor 335 with the remainder of the image 312 from the image processor 307, such that the image displayed at the display 317 comprises a combination of the local and remote results.

Figure 4:
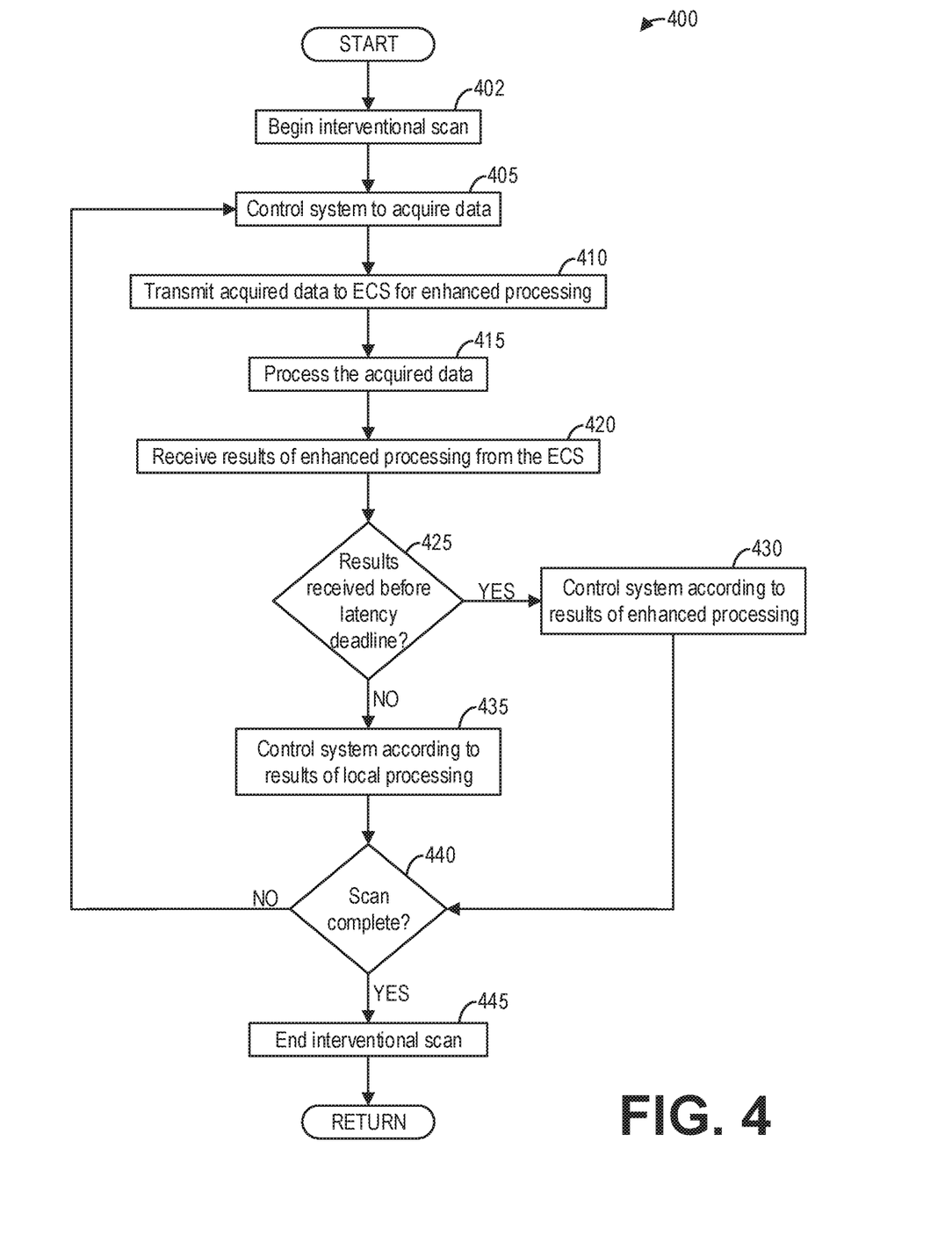
FIG. 4 shows a high-level flow chart illustrating an example method for enhanced processing with a remote computing system during an interventional scan according to an embodiment.
Figure 5:
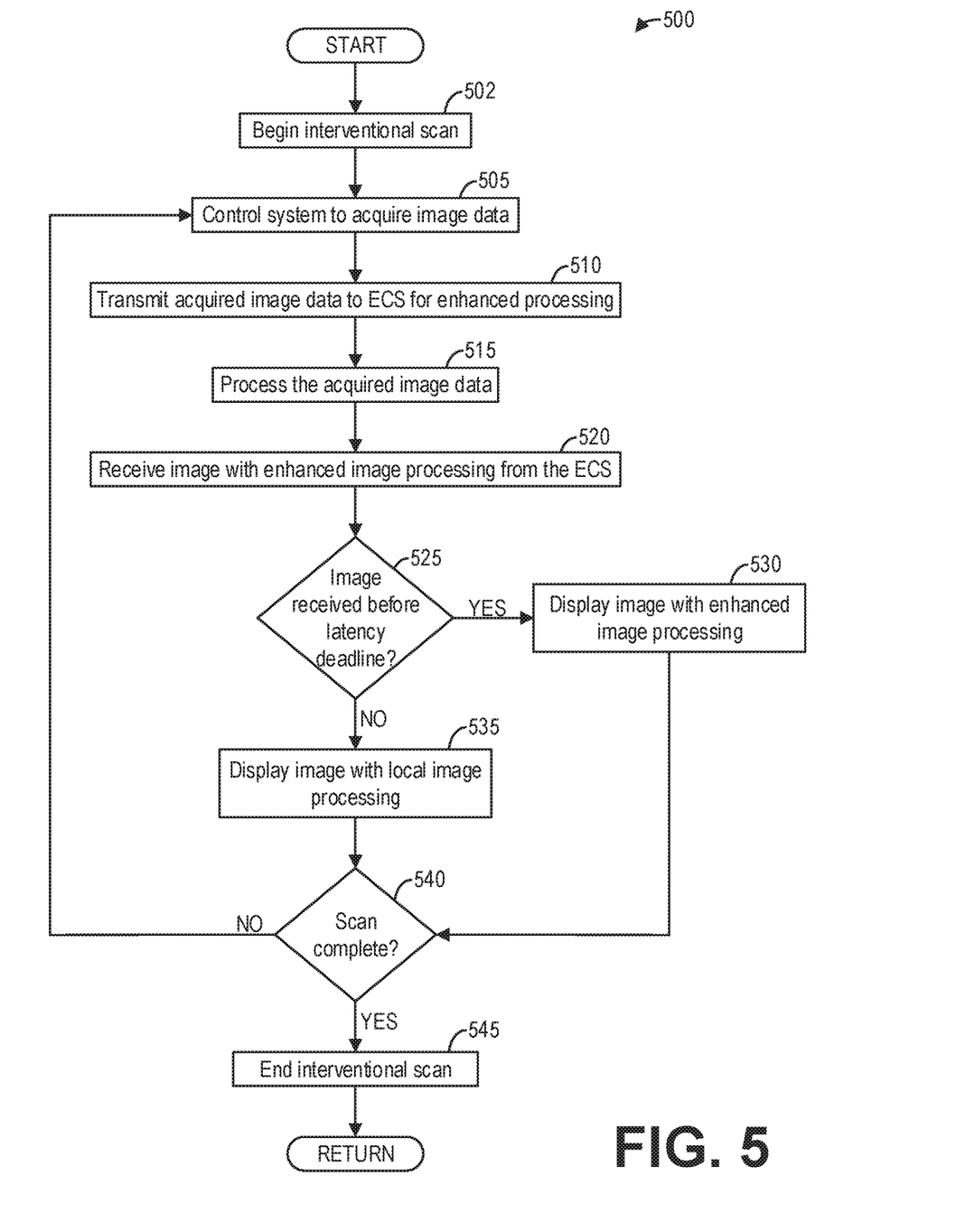
FIG. 5 shows a high-level flow chart illustrating an example method for enhanced image processing with a remote computing system during an interventional scan according to an embodiment.

FIG. 4 shows a high-level flow chart illustrating an example method 400 for enhanced processing with a remote computing system during an interventional scan according to an embodiment. In particular, method 400 relates to remotely processing data and controlling an imaging system with the results of the remote processing if the results are received within a latency deadline. Method 400 is described with regard to the systems and components of FIGS. 1-3, though it should be appreciated that the method 400 may be implemented with other systems and components without departing from the scope of the present disclosure. Method 400 may be implemented as executable instructions in non-transitory memory, such as memory 104, and executable by a controller or processor, such as processor 103, of an imaging system for interventional imaging such as imaging system 101.

Method 400 begins at 402. At 402, method 400 begins an interventional scan. At 405, method 400 controls the imaging system 101 to acquire data. For example, the data may comprise image data, and thus method 400 controls the scanner 105 to acquire image data. In the context of x-ray fluoroscopy, for example, method 400 controls an x-ray source of the scanner 105 to emit x-rays towards a subject, and further receives x-rays detected by an x-ray detector of the scanner 105. In other examples, method 400 additionally or alternatively controls the imaging system 101 to acquire data that is not image data during the scan. For example, method 400 may acquire position data of components of the scanner 105, such as the position of the x-ray source and/or the x-ray detector relative to the patient.

After acquiring the data, method 400 continues to 410. At 410, method 400 transmits the acquired data to the ECS 110 for enhanced processing. Method 400 may transmit, via a data distributor such as data distributor 205, the acquired data to the ECS 110 via the network 120. Method 400 may transmit the data as soon as it is acquired and/or generated by the imaging system 101. Further, prior to transmitting the acquired data to the ECS 110, method 400 may tag the acquired data with relevant information such as a timestamp of acquisition or generation of the data, acquisition parameters for acquiring the data, and an identifier of the data. In this way, the data may be used by the ECS 110 for processing the data and/or the imaging system 101 may correlate, according to the identifier for example, the data processed by the ECS 110 with the same data processed locally.

In addition to transmitting the acquired data to the ECS 110 for remote processing, method 400 processes the acquired data at 415. The processing of the acquired data may be configured to guarantee latency, such that the processing of the acquired data may be accomplished in real-time in accordance with the computing capabilities of the imaging system 101. For example, if the acquired data comprises position information of components of the scanner 105, the processing may comprise anti-collision management and/or motion control for predicting relative positions of the components of the scanner 105 to the patient being scanned and the operator of the imaging system 101. In such an example, method 400 may utilize a simplified model of the components such that prediction calculations may be accomplished within a threshold duration or latency. As another example, if the acquired data comprises image data, the processing may include a basic noise reduction applied to the image data configured to be accomplished within the threshold duration.

The remote processing of the acquired data being carried out by the ECS 110, in contrast, comprises enhanced processing that utilizes computing resources greater than the computing resources allocable by the processing subsystem 106 of the imaging system 101. For example, in examples where the processing of the processing subsystem 106 comprises anti-collision management and/or motion control, the enhanced processing by the data or image processor of the ECS 110 may use three-dimensional wireframe models with a finer polygonal mesh than the processing subsystem 106 for performing the anti-collision management and/or motion control.

Continuing at 420, method 400 receives the results of the enhanced processing from the ECS 110. Method 400 receives the results, for example, via the network 120. The results may include or be tagged with the identifier used to tag the acquired data prior to transmission at 410, such that method 400 may identify or verify that the received results correspond to the acquired data transmitted at 410.

At 425, method 400 determines if the results were received from the ECS 110 before a latency deadline. As discussed hereinabove, in one example, the latency comprises the time difference between receiving the local results generated at 415 and the remote results at 420. In this example, the latency deadline comprises a threshold duration beginning when the local processing at 415 is complete. In an alternate example, the latency comprises the time difference between transmitting the acquired data at 410 and receiving the results at 420. In this example, the latency deadline comprises a threshold duration beginning when the acquired data is transmitted to the ECS 110 at 410. In either example, the latency deadline may be predetermined or configured such that there is no human-perceivable difference if the local result or the remote result is used to control the imaging system 101. The latency deadline may therefore comprise a duration ranging from 40 milliseconds to 100 milliseconds, as an illustrative example, though it should be appreciated that in some examples the latency deadline may be greater than 100 milliseconds.

If the results are received before the latency deadline ("YES"), method 400 continues to 430. At 430, method 400 controls the imaging system 101 according to the results of the enhanced processing by the ECS 110. For example, if the results of the enhanced processing comprise an enhanced image, method 400 may display the enhanced image via a display device such as display 108 of the imaging system 101. As another example, if the results of the enhanced processing comprise enhanced motion control commands for anti-collision management, method 400 may control one or more components of the scanner 105 according to the enhanced motion control commands.

However, if the results are not received before the latency deadline ("NO"), method 400 continues to 435. At 435, method 400 controls the imaging system according to the results of the local processing at 415. For example, if the results of the local processing at 415 comprises an image, method 400 may display the image processed at 415 via the display 108. As another example, if the results of the local processing at 415 comprise motion control commands determined with a simpler model than the enhanced motion control commands from the ECS 110, method 400 may control one or more components of the scanner 105 according to the motion control commands. Thus, if the results of the enhanced processing from the ECS 110 received at 420 are received after the latency deadline, method 400 uses the results of the local processing instead.

After controlling the imaging system 101 according to the results of the enhanced processing at 430, or controlling the imaging system 101 according to the results of the local processing at 435, method 400 continues to 440. At 440, method 400 determines if the scan is complete. If the scan is not complete ("NO"), method 400 returns to 405 to continue controlling the imaging system 101 to acquire data. However, if the scan is complete ("YES"), method 400 continues to 445. At 445, method 400 ends the interventional scan. Method 400 then returns.

The local and remote processing may comprise image processing, as described hereinabove with regard to FIG. 3. For example, FIG. 5 shows a high-level flow chart illustrating an example method 500 for enhanced image processing with a remote computing system during an interventional scan according to an embodiment. In particular, method 500 relates to processing an image remotely and displaying the remotely-processed image if the image is received within a latency deadline. Method 500 is described with regard to the systems and components of FIGS. 1-3 though it should be appreciated that the method 500 may be implemented with other systems and components without departing from the scope of the present disclosure. Method 500 may be implemented as executable instructions in non-transitory memory, such as memory 104, and executable by a controller or processor, such as processor 103, of an imaging system for interventional imaging such as imaging system 101 to perform the actions described herein.

Method 500 begins at 502. At 502, method 500 begins an interventional scan. Continuing at 505, method 500 controls the imaging system to acquire image data. For example, method 500 controls a scanner 105 of the imaging system 101 to acquire image data. In the context of x-ray fluoroscopy, for example, method 500 controls an x-ray source of the scanner 105 to emit x-rays towards a subject, and further receives x-rays detected by an x-ray detector of the scanner 105.

At 510, method 500 transmits acquired image data to the ECS 110 for enhanced image processing. Further, prior to transmitting the acquired data to the ECS 110, method 500 may tag the acquired image data with relevant information such as a timestamp of acquisition of the image data, acquisition parameters for acquiring the image data, and an identifier of the image data.

As discussed hereinabove, the enhanced image processing may include image processing that a local processor of the imaging system 101 is not capable of performing with a guaranteed latency. Such image processing may include noise reduction, enhanced image quality characteristics, interventional device visibility enhancement, image registration and fusion, and so on as non-limiting examples. The remote computing system or ECS 110 thus performs the enhanced image processing of the image data transmitted to the ECS 110. Meanwhile, at 515, method 500 locally processes the acquired image data with real-time, guaranteed latency processing with nominal image quality characteristics.

Continuing at 520, method 500 receives an image with enhanced image processing from the ECS 110. At 525, method 500 determines if the image is received from the ECS 110 before a latency deadline. As discussed hereinabove, the latency deadline may comprise a duration starting after method 500 locally processes the acquired image data at 515. Thus, the latency of the remote processing comprises the elapsed time between 515 and 520. The latency deadline may range from 50 milliseconds to 500 milliseconds, and may specifically comprise, for example 80 milliseconds. The latency deadline may be determined according to human perceptibility of a lag in the display of images or frames, for example, on the display. As an illustrative example, film cameras may feature a frame rate of 24 frames per second, whereas in animated films each animated frame may be shot twice or for two frames. For a film camera, the duration of each frame is approximately 42 milliseconds, while the duration of an animated frame in an animated film may be approximately 84 milliseconds. The latency deadline may thus be determined according to similar considerations.

Referring again to 525, if method 500 receives the image with enhanced image processing from the ECS at 520 prior to the latency deadline ("YES"), method 500 continues to 530. At 530, method 500 displays the enhanced image or the image with the enhanced image processing from the ECS 110. The enhanced image may be displayed, for example, via the display 108 of the imaging system 101.

However, if method 500 does not receive the image with enhanced image processing prior to the latency deadline ("NO"), method 500 instead proceeds from 525 to 535. At 535, method 500 displays the image with local processing from 515. Thus, if the enhanced image from the ECS is not received prior the latency deadline, the native image stream is directed to the display for guidance of the intervention. Further, in some examples, method 500 may display an indication to the user that the native or local image stream is being displayed instead of the enhanced image stream.

After displaying the image with enhanced image processing at 530 or displaying the image with local image processing at 535, method 500 continues to 540. At 540, method 500 determines if the scan is complete. If the scan is not complete ("NO"), method 500 returns to 505 to continue controlling the imaging system 101 to acquire image data. In this way, method 500 may continuously iterate during an interventional scan such that an enhanced image may be processed for acquired data during the scan and displayed, while the native or nominal image is displayed during instances wherein the latency or throughput of the ECS 110 falls behind the latency deadline. The real-time display to the operator is thus effectively uninterrupted regardless of the bandwidth of the network or the ECS 110.

Once the scan is determined to be complete at 540 ("YES"), method 500 continues to 545. At 545, method 500 ends the interventional scan. Method 500 then returns.

Thus, in one embodiment, a method for an imaging system comprises acquiring image data with a scanner of the imaging system, transmitting the image data to a remote computing system positioned away from the imaging system, locally processing the image data at the imaging system, receiving enhanced image data from the remote computing system, displaying the enhanced image data if the enhanced image data is received within a latency deadline, and displaying the locally-processed image data if the enhanced image data is not received within the latency deadline.

As described with regard to FIG. 4, the scope of the present disclosure extends beyond local and remote image processing. For example, any type of data processing normally embedded in an imaging system, such as anti-collision management, patient dose mapping, exposure control, motion control, and so on may be performed by the ECS 110. Remote processing by the ECS 110 is especially well suited for computer-intensive processing.

Figure 6:
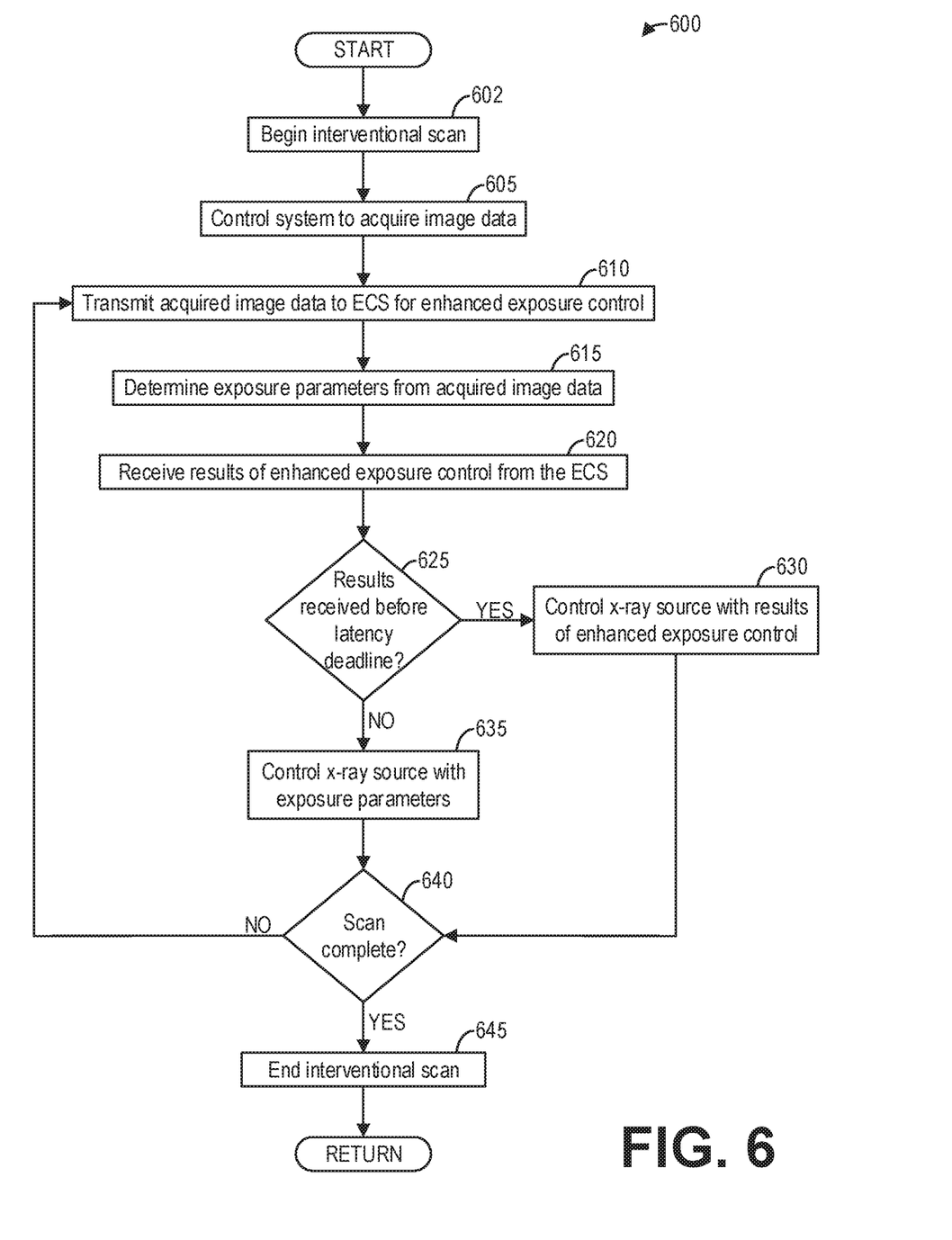
FIG. 6 shows a high-level flow chart illustrating an example method for enhanced control of an x-ray source with a remote computing system during an interventional scan according to an embodiment.

As an illustrative example, FIG. 6 shows a high-level flow chart illustrating an example method 600 for enhanced control of an x-ray source with a remote computing system during an interventional scan according to an embodiment. In particular, method 600 relates to using enhanced exposure control for controlling an x-ray source during an interventional responsive to receiving the results of the enhanced exposure control from an ECS prior to a latency deadline. Method 600 is described with regard to the systems and components of FIGS. 1 and 2, though it should be appreciated that the method 600 may be implemented with other systems and components without departing from the scope of the present disclosure. Method 600 may be stored as executable instructions in non-transitory memory, such as memory 104, and executed by a controller or processor, such as processor 103, of an interventional imaging system such as imaging system 101 for performing the actions described herein.

Method 600 begins at 602. At 602, method 600 begins an interventional scan. Continuing at 605, method 600 controls the imaging system to acquire image data. For example, method 600 controls the scanner 105 of the imaging system 101 to acquire image data. In the context of x-ray fluoroscopy, for example, method 600 controls an x-ray source of the scanner 105 to emit x-rays towards a subject, and further receives x-rays detected by an x-ray detector of the scanner 105.

At 610, method 600, method 600 transmits or streams, over the network 120, the acquired image data to the ECS 110 for remote processing. Meanwhile, at 615, method 600 locally determines exposure parameters for an x-ray source of the imaging system 101 from the acquired image data. In some examples, method 600 determines exposure parameters for the x-ray source initially during the interventional scan and uses these exposure parameters to control the x-ray source throughout the interventional scan. In other examples, method 600 determines updated exposure parameters for the x-ray source according to image data, for example to adjust the contrast responsive to the image data.

The ECS 110, meanwhile, performs enhanced exposure control based on the image data. For example, the enhanced exposure control may include patient dose mapping and/or may use a more sophisticated, computationally-expensive technique for exposure control that, for example, may adjust exposure parameters to minimize noise artifacts detected in the image data. In general, the enhanced exposure control comprises a technique for exposure control that is too computationally expensive for the computing resources of the imaging system 101 to perform the technique with a guaranteed latency.

Continuing at 620, method 600 receives the results of the enhanced exposure control from the ECS 110. At 625, method 600 determines if the results are received before a latency deadline. The latency deadline may be determined, for example, according to the desired frame rate of the live image feed via the display as described hereinabove with regard to FIG. 5.

If the results are received before the latency deadline ("YES"), method 600 continues to 630. At 630, method 600 controls the x-ray source of the scanner 105 with the results of the enhanced exposure control. However, if the results are not received before the latency deadline ("NO"), method 600 continues to 635. At 635, method 600 controls the x-ray source with the exposure parameters determined at 615.

After controlling the x-ray source with the results of the enhanced exposure control or the locally-determined exposure parameters, method 600 continues to 640. At 640, method 600 determines if the interventional scan is complete. If the scan is not complete ("NO"), method 600 returns to 605 to continue the scan by transmitting the acquired image data resulting from the control of the x-ray source with the remotely or locally-determined exposure control to the ECS for additional enhanced exposure control. In this way, the exposure control may be dynamically adjusted throughout the interventional scan according to either the remote exposure control or the local exposure control. Accordingly, the image quality as well as patient dose may be dynamically managed and optimized throughout the scan.

Once the scan is complete ("YES"), method 600 continues to 645. At 645, method 600 ends the interventional scan. Method 600 then returns.

Figure 7:
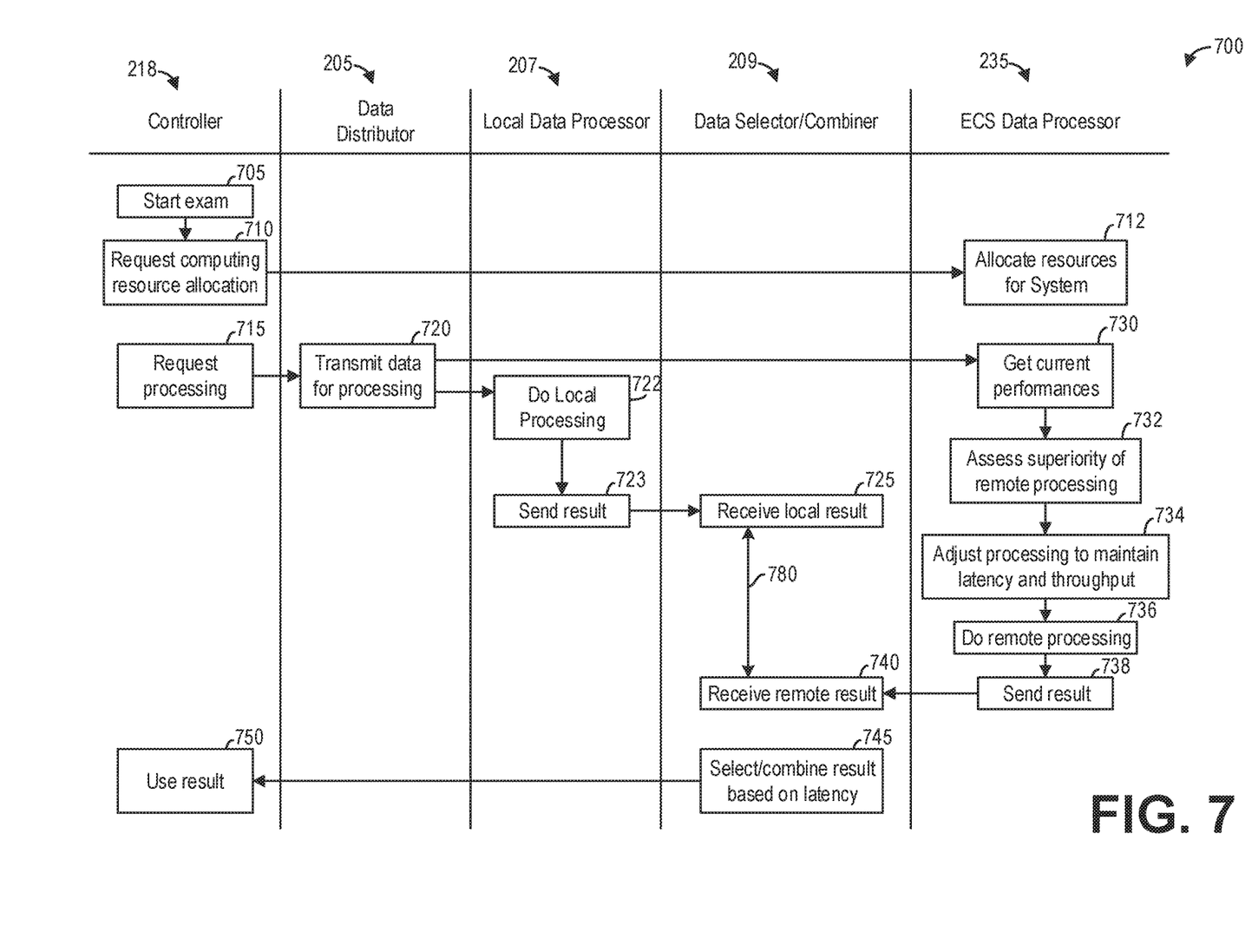
FIG. 7 shows a high-level swim-lane flow chart illustrating an example method for selecting and combining local and remote processing results during an examination according to an embodiment.

FIG. 7 shows a high-level swim-lane flow chart illustrating an example method 700 for selecting and combining local and remote processing results during an examination according to an embodiment. In particular, method 700 depicts the various interactions between components of an imaging system. For example, with regard to the system of FIG. 1, method 700 depicts the interactions between the processor 103 of the imaging system 101, the processing subsystem 106, and the ECS 110. With regard to the systems of FIGS. 2 and 3, method 700 depicts the interactions between the controller 218 of the imaging system 201 or the processor 103 of the imaging system 101, the data distributor 205 of the data processing subsystem 200 or the image distributor 305 of the image processing subsystem 300, the local data processor 207 of the data processing subsystem 200 or the local image processor 307 of the image processing subsystem 300, the data selector/combiner 209 of the data processing subsystem 200 or the image selector/combiner 309 of the image processing subsystem 300, and the data processor 235 of the ECS 230 or the image processor 335 of the ECS 330. For simplicity, method 700 is specifically described with regard to the systems and components of FIG. 2, though as mentioned above it should be appreciated that the method 700 may be implemented with other systems and components, such as the systems and components of FIGS. 1 and 3, without departing from the scope of the present disclosure.

Method 700 begins at 705. At 705, the controller 218 starts an interventional examination or scan. To that end, the imaging system 201 begins acquiring data, for example via a scanner such as scanner 105. Meanwhile, at 710, the controller 218 requests allocation of remote computing resources for the examination. The request is transmitted to the data processor 235 of the ECS 230. At 712, the data processor 235 of the ECS 230 allocates resources for the imaging system 201 according to the request. For example, if dynamic allocation mechanisms are available, the imaging system 101 and/or the ECS 230 may request network resources for a given examination to ensure throughput/bandwidth and latency.

After requesting computing resources, at 715, the controller 218 requests processing of the data acquiring or generated during the examination. The request is submitted to the data distributor 205 of the data processing subsystem 200. Responsive to the request for processing at 715, at 720, the data distributor 205 transmits the data for processing to both the data processor 235 and the local data processor 207. The local data processor 207 performs the local processing at 722, and sends the results at 723 to the data selector/combiner 209. The data selector/combiner 209 receives the local result at 725.

Meanwhile, at 730, the data processor 235 of the ECS 230 evaluates current performances of the data processor 235. Additionally, the data processor 235 may evaluate the current performance of the data processor 207 with respect to the data processor 235. At 732, the data processor 235 assess the "superiority" of the remote processing by the data processor 235 with regard to the local data processor 207. As an example, the data processor 235 may determine whether previous remote results were of increased quality or utility with respect to the local result of the imaging system 201. Additionally or alternatively, the data processor 235 may determine whether the remote processing in a previous iteration was received in sufficient time for using the remote result rather than the local result. The data processor 235 thus may determine or assess the superiority of the remote processing according to the current performances of the data processor 235 and/or the local data processor 207.

As another example, the data processor 235 may include or communicate with a knowledge database of system quality for each processing type and each system version. For example, the knowledge database may indicate compatibility for particular processing actions between imaging systems and the ECS. The data processor 235 may thus not perform enhanced processing if the local data processing of the imaging system 101 is more enhanced or sophisticated than the data processing offered by the data processor 235. In such examples, the data processor 235 may transmit an interoperability certificate or credentials to the imaging system 101 such that the imaging system 101 may "trust" the remote computer to deliver results of increased quality versus the locally-generated results. Such an interoperability certificate may comprise a simple token exchanged between the imaging system 101 and the ECS 230 within an API call, which would uniquely identify the imaging system and allow the ECS 230 to provide the interoperability credentials.

Further, at 734, the data processor 235 optionally adjusts the processing to maintain latency and throughput. For example, as the data processor 730 evaluates current performances at 730 and assess superiority of remote processing at 732, the ECS 230 is thus configured to monitor performance and resource availability (including availability of the network 220) in real time. If resources degrade to the extent that communication latency cannot be maintained, the data processor 235 of the ECS 230 may adjust the remote processing to maintain latency and throughput at the expense of quality of the result. For example, in image processing, the resolution may be degraded in most of the image, except in the area of most interest (usually the center of the image, or the ROI may be inferred by the presence of specific features, or specified by the user, and so on). In collision management or patient dose mapping, a coarser three-dimensional mesh may be used to model the various mechanical elements of the scanner 105 and the patient.

At 736, the data processor 235 performs the remote processing. The data processor 235 may perform the remote processing with adjustments made at 734 to maintain latency and throughput. Once the remote processing is complete, at 738, the data processor 235 sends or transmits the result of the remote processing to the data selector/combiner 209.

The data selector/combiner 209 thus receives the remote result at 740. As depicted, the latency 780 of the remote processing comprises the duration between receiving the local result at 725 and receiving the remote result at 740. The data selector/combiner 209 selects and/or combines the result(s) according to the latency 780. The selected or combined result is then output to the controller 218, which uses the result at 750 to control the imaging system 201.

A technical effect of the present disclosure includes the real-time control of an imaging system according to remotely processed results. Another technical effect of the disclosure includes the real-time display of an enhanced image acquired by an imaging system and processed at a computing system positioned remotely to the imaging system. Yet another technical effect of the disclosure includes the display of a native image stream when latency of remote processing surpasses a latency threshold or deadline. Another technical effect of the disclosure includes the real-time adjustment of x-ray source exposure parameters according to remote processing of image data at a computing system remote from the imaging system.

In one embodiment, a method for an imaging system comprises, during a scan, transmitting data to a remote computing system, controlling the imaging system according to results of remote processing of the data via the remote computing system responsive to receiving the results of the remote processing before a latency deadline, and controlling the imaging system according to results of local processing at the imaging system responsive to receive the results of the remote processing after the latency deadline.

In a first example of the method, the method further comprises acquiring image data via a scanner of the imaging system, wherein the data transmitted to the remote computing system comprises the image data. In a second example of the method optionally including the first example, the results of the remote processing comprise an image with enhanced image processing, and controlling the imaging system according to the results of the remote processing comprises displaying, via a display device of the imaging system, the image with the enhanced image processing. In a third example of the method optionally including one or more of the first and second examples, the results of the local processing at the imaging system comprises an image with nominal image processing, and wherein controlling the imaging system according to the results of the local processing comprises displaying, via the display device, the image with the nominal image processing. In a fourth example of the method optionally including one or more of the first through third examples, the results of the remote processing comprise enhanced exposure control, and controlling the imaging system according to the results of the remote processing comprises controlling an x-ray source of the imaging system according to the enhanced exposure control. In a fifth example of the method optionally including one or more of the first through fourth examples, the results of the local processing comprise nominal exposure control, and controlling the imaging system according to the results of the local processing comprises controlling the x-ray source according to the nominal exposure control. In a sixth example of the method optionally including one or more of the first through fifth examples, the method further comprises recording positions of one or more components of the imaging system during the scan, wherein the data comprises the recorded positions. In a seventh example of the method optionally including one or more of the first through sixth examples, the results of the remote processing comprises enhanced anti-collision management and enhanced motion control of the one or more components, and controlling the imaging system according to the results of the remote processing comprises controlling motion of the one or more components according to the enhanced anti-collision management and the enhanced motion control. In an eighth example of the method optionally including one or more of the first through seventh examples, the results of the local processing comprises nominal anti-collision management and nominal motion control of the one or more components, and controlling the imaging system according to the results of the local processing comprises controlling the motion of the one or more components according to the nominal anti-collision management and the nominal motion control. In a ninth example of the method optionally including one or more of the first through eighth examples, the latency deadline comprises a duration between obtaining the results of the local processing and receiving the results of the remote processing. In a tenth example of the method optionally including one or more of the first through ninth examples, the latency deadline ranges from 50 milliseconds to 500 milliseconds.

In another embodiment, a method for an imaging system comprises acquiring, via a scanner of the imaging system, image data of a subject, transmitting, via a network, the image data to a remote computing system communicatively coupled to the imaging system, processing the image data to generate a nominal image, receiving an enhanced image from the remote computing system, the enhanced image generated by the remote computing system by enhanced image processing of the image data, displaying, via a display device of the imaging system, the enhanced image responsive to receiving the enhanced image from the remote computing system before a latency deadline, and displaying, via the display device, the nominal image responsive to not receiving the enhanced image before the latency deadline.

In a first example of the method, the method further comprises selectively combining the enhanced image and the nominal image into a combined image, and wherein displaying the enhanced image comprises displaying, via the display device, the combined image. In a second example of the method optionally including the first example, selectively combining the enhanced image and the nominal image comprises combining a region of interest of the enhanced image with a remainder of the nominal image not including the region of interest. In a third example of the method optionally including one or more of the first and second examples, the method further comprises displaying, via the display device, an indication that the nominal image is being displayed responsive to not receiving the enhanced image before the latency deadline.

In yet another embodiment, a system comprises an imaging system comprising a scanner for acquiring image data and a processor for controlling the imaging system, and a remote computing system communicatively coupled to the imaging system via a network, the remote computing system comprising a remote processor. The processor of the imaging system is configured with executable instructions in non-transitory memory of the imaging system that when executed causes the processor to: transmit data acquired or generated by the imaging system to the remote computing system via the network; and process the data to generate a locally-processed result. The remote processor of the remote computing system is configured with executable instructions in non-transitory memory of the remote computing system that when executed causes the remote processor to receive the data from the imaging system, process the data with enhanced processing to generate an enhanced result, and transmit the enhanced result to the imaging system via the network. The processor is further configured with instructions in the non-transitory memory of the imaging system that when executed causes the processor to receive the enhanced result from the remote computing system, control the imaging system according to the enhanced result if the enhanced result is received before a latency deadline, and control the imaging system according to the locally-processed result if the enhanced result is received after the latency deadline.

In a first example of the system, the remote processor is further configured with instructions in the non-transitory memory of the remote computing system that when executed causes the remote processor to evaluate current performance of one or more of the remote computing system and the network, and adjust the remote processing to maintain latency and throughput. In a second example of the system optionally including the first example, the data comprises the image data, the locally-processed result comprises a locally-processed image, the enhanced result comprises an enhanced image, controlling the imaging system according to the enhanced result comprises displaying, via a display device of the imaging system, the enhanced image, and controlling the imaging system according to the locally-processed result comprises displaying, via the display device, the locally-processed image. In a third example of the system optionally including one or more of the first and second examples, the processor is further configured with instructions in the non-transitory memory of the imaging system that when executed causes the processor to selectively combine the enhanced image and the locally-processed image into a combined image, and display, via the display device, the combined image. In a fourth example of the system optionally including one or more of the first through third examples, the latency deadline comprises a threshold duration after generating the locally-processed result.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
   during a scan of an internal anatomy, transmitting data to a remote computing system;
   controlling the imaging system according to results of remote processing of the data via the remote computing system responsive to receiving the results of the remote processing before a latency deadline;
   controlling the imaging system according to results of local processing of the data at the imaging system responsive to receiving the results of the remote processing after the latency deadline;
   wherein the results of local processing comprises a locally-processed image, wherein the results of remote processing comprises an enhanced image; and
   wherein the method further comprises selectively combining the enhanced image and the locally-processed image into a combined image, and display, via the display device, the combined image.

2. The method of claim 1, further comprising acquiring image data via a scanner of the imaging system, wherein the data transmitted to the remote computing system comprises the image data.

3. The method of claim 2, wherein the results of the remote processing comprise an image with enhanced image processing, and wherein controlling the imaging system according to the results of the remote processing comprises displaying, via a display device of the imaging system, the image with the enhanced image processing.

4. The method of claim 3, wherein the results of the local processing at the imaging system comprises an image with nominal image processing, and wherein controlling the imaging system according to the results of the local processing comprises displaying, via the display device, the image with the nominal image processing.

5. The method of claim 2, wherein the results of the remote processing comprise enhanced exposure control, and wherein controlling the imaging system according to the results of the remote processing comprises adjusting exposure parameters of an x-ray source.

6. The method of claim 5, wherein the results of the local processing comprise nominal exposure control, and wherein controlling the imaging system according to the results of the local processing comprises controlling the x-ray source according to the nominal exposure control.

7. The method of claim 5, further comprising recording positions of one or more components of the imaging system during the scan, wherein the data comprises the recorded positions including position of the x-ray source relative to a patient.

8. The method of claim 7, wherein the results of the remote processing comprises enhanced anti-collision management and enhanced motion control of the one or more components, and wherein controlling the imaging system according to the results of the remote processing comprises controlling motion of the one or more components according to the enhanced anti-collision management and the enhanced motion control.

9. The method of claim 8, wherein the results of the local processing comprises nominal anti-collision management and nominal motion control of the one or more components, and wherein controlling the imaging system according to the results of the local processing comprises controlling the motion of the one or more components according to the nominal anti-collision management and the nominal motion control.

10. The method of claim 1, wherein the latency deadline comprises a duration between obtaining the results of the local processing and receiving the results of the remote processing.

11. The method of claim 10, wherein the latency deadline ranges from 50 milliseconds to 500 milliseconds.

12. A method for an imaging system, comprising:
acquiring, via a scanner of the imaging system, image data of an internal anatomy of a subject;
transmitting, via a network, the image data to a remote computing system communicatively coupled to the imaging system;
processing the image data to generate a nominal image;
receiving an enhanced image from the remote computing system, the enhanced image generated by the remote computing system by enhanced image processing of the image data;
displaying, via a display device of the imaging system, the enhanced image responsive to receiving the enhanced image from the remote computing system before a latency deadline; and
displaying, via the display device, the nominal image responsive to not receiving the enhanced image before the latency deadline; and
wherein the method further comprises selectively combining the enhanced image and the nominal image into a combined image, and display, via the display device, the combined image.

13. The method of claim 12, wherein selectively combining the enhanced image and the nominal image comprises combining a region of interest of the enhanced image with a remainder of the nominal image not including the region of interest.

14. The method of claim 12, further comprising displaying, via the display device, an indication that the nominal image is being displayed responsive to not receiving the enhanced image before the latency deadline.

15. A system, comprising:
an imaging system comprising a scanner for acquiring image data of an internal anatomy of a subject and a processor for controlling the imaging system; and
a remote computing system communicatively coupled to the imaging system via a network, the remote computing system comprising a remote processor;
wherein the processor of the imaging system is configured with executable instructions in non-transitory memory of the imaging system that when executed causes the processor to:
transmit data acquired or generated by the imaging system to the remote computing system via the network; and
process the data to generate a locally-processed result;
wherein the remote processor of the remote computing system is configured with executable instructions in non-transitory memory of the remote computing system that when executed causes the remote processor to:
receive the data from the imaging system;
process the data with enhanced processing to generate an enhanced result; and
transmit the enhanced result to the imaging system via the network; and
wherein the processor is further configured with instructions in the non-transitory memory of the imaging system that when executed causes the processor to:
receive the enhanced result from the remote computing system;
control the imaging system according to the enhanced result if the enhanced result is received before a latency deadline;
control the imaging system according to the locally-processed result if the enhanced result is received after the latency deadline;
wherein the locally-processed result comprises a locally-processed image, wherein the enhanced result comprises an enhanced image; and
wherein the processor is further configured with instructions in the non-transitory memory of the imaging system that when executed causes the processor to selectively combine the enhanced image and the locally-processed image into a combined image, and display, via the display device, the combined image.

16. The system of claim 15, wherein the remote processor is further configured with instructions in the non-transitory memory of the remote computing system that when executed causes the remote processor to evaluate current performance of one or more of the remote computing system and the network, and adjust the remote processing to maintain latency and throughput.

17. The system of claim 15, wherein controlling the imaging system according to the enhanced result comprises displaying, via a display device of the imaging system, the enhanced image, and wherein controlling the imaging system according to the locally-processed result comprises displaying, via the display device, the locally-processed image.

18. The system of claim 15, wherein the latency deadline comprises a threshold duration after generating the locally-processed result.

19. The method of claim 2, wherein the results of the remote processing comprise an image with interventional device visibility enhancement.

20. The method of claim 3, wherein enhanced image processing is applied only to the center region of the image to meet the latency deadline.

* * * * *